United States Patent
Okuda et al.

(10) Patent No.: US 6,855,930 B2
(45) Date of Patent: Feb. 15, 2005

(54) DEFECT INSPECTION APPARATUS AND DEFECT INSPECTION METHOD

(75) Inventors: Hirohito Okuda, Yokohama (JP); Yuji Takagi, Kamakura (JP); Toshifumi Honda, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/256,585

(22) Filed: Sep. 27, 2002

(65) Prior Publication Data

US 2003/0118149 A1 Jun. 26, 2003

(30) Foreign Application Priority Data

Sep. 28, 2001 (JP) .................................... 2001-302108

(51) Int. Cl.⁷ ............................................... G01N 23/00
(52) U.S. Cl. ...................................... 250/310; 378/45
(58) Field of Search ........................... 378/44, 45, 46, 378/49, 58; 250/305, 310, 311

(56) References Cited

U.S. PATENT DOCUMENTS

| | | | | | |
|---|---|---|---|---|---|
| 5,369,275 A | * | 11/1994 | Usui et al. | ................... | 250/310 |
| 5,659,174 A | * | 8/1997 | Kaneoka et al. | ............. | 250/310 |
| 5,777,327 A | * | 7/1998 | Mizuno | ....................... | 250/310 |
| 5,801,382 A | * | 9/1998 | Noda et al. | ................... | 250/310 |
| 6,043,486 A | * | 3/2000 | Hossain | .................... | 250/252.1 |
| 6,072,178 A | * | 6/2000 | Mizuno | ....................... | 250/310 |
| 6,266,390 B1 | * | 7/2001 | Sommer et al. | ............... | 378/45 |
| 6,407,386 B1 | * | 6/2002 | Dotan et al. | ................. | 250/310 |
| 6,448,555 B1 | * | 9/2002 | Hosokawa | .................... | 250/310 |
| 6,753,525 B1 | * | 6/2004 | Testoni | ........................ | 250/310 |

FOREIGN PATENT DOCUMENTS

JP         10-27833         1/1998

* cited by examiner

*Primary Examiner*—Allen C. Ho
(74) *Attorney, Agent, or Firm*—Townsend and Townsend and Crew LLP

(57) ABSTRACT

An apparatus and a method for automatically inspecting a defect by an electron beam using an X-ray detector. The composition of a defective portion is analyzed with higher rapidity and the cause of the defect is easily and accurately determined based on an X-ray spectrum. The X-ray spectrum and the image of foreign particles formed on a process QC wafer are registered as reference data, and the defects generated on a process wafer are classified by collation with the reference data. The use of both the X-ray spectrum and the detected image optimizes the operating conditions for X-ray detection. A defect of which the X ray is to be detected is selected based on the result of classification of defect images automatically collected, and the defect is classified according to the features including both the composition and the external appearance.

9 Claims, 17 Drawing Sheets

54 DEFLECTION SYSTEM CONTROL CIRCUIT
57: VACUUM SYSTEM
58 VACUUM CONTROL CIRCUIT
512 : X-RAY SPECTROMETER
513, 515 : SIGNAL PROCESSING CIRCUIT
514 :SECONDARY ELECTRON DETECTOR

FIG. 7

ADR/ADC
- IMAGING MAGNIFICATION
- ACCEL VOLTAGE
- PROBE CURRENT
- ELECTRON BEAM DIA

EDX

| | LIGHT ELEMENT | HEAVY ELEMENT |
|---|---|---|
| ACCEL VOLTAGE | | |
| PROBE CURRENT | | |
| ELECTRON BEAM DIA | | |

DETECTED IMAGE

EDX WAVEFORM

EDX SAMPLING CONDITIONS

| | DEFECT TYPE | SIZE | DESIGNATED ORDER |
|---|---|---|---|
| 1 | FOREIGN PARTICLE A | | ONE UPPER CLASS |
| 2 | FOREIGN PARTICLE B | | ONE UPPER CLASS |
| 3 | FOREIGN PARTICLE C | | ONE UPPER CLASS |
| 4 | | | |
| 5 | | | |

DESIGNATED FORMULA: 1+2+3

INSPECTED WAFER

| TYPE | PROCESS | L α D | Wafer ID | | | | |
|---|---|---|---|---|---|---|---|
| | | | | | | | |
| | | | | | | | |
| | | | | | | | |
| | | | | | | | |
| | | | | | | | |

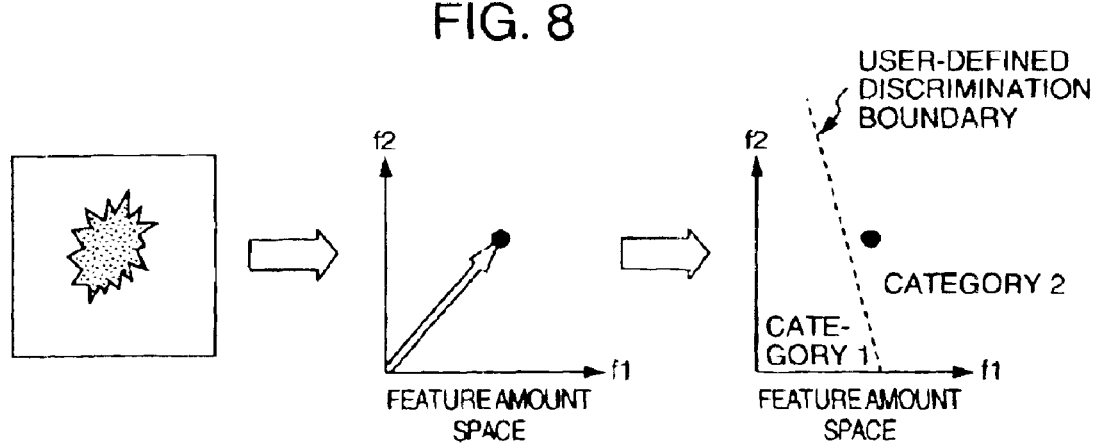

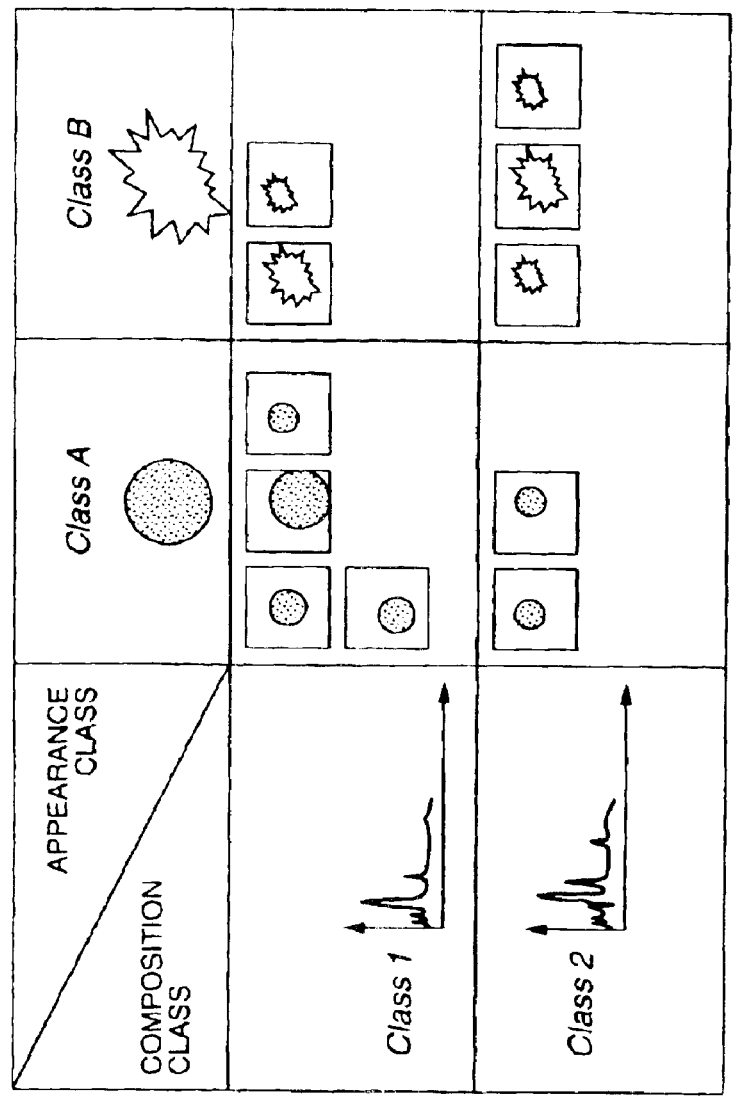

DEFECT INSPECTION APPARATUS AND DEFECT INSPECTION METHOD

BACKGROUND OF THE INVENTION

The present invention relates to a defect inspection apparatus and a defect inspection method, or in particular to a defect inspection apparatus and a defect inspection method using a technique suitable for inspection and analysis of a defect generated on a semiconductor wafer in the process of fabricating a semiconductor electronic circuit, in which an electron beam is radiated on a defective portion and the X-ray spectrum generated is analyzed.

(1) Outline of Defect Analysis by EDX

A method called EDX (Energy Dispersion X-ray Spectrum) is known as a conventional technique for analyzing the cause of the foreign particles generated on a semiconductor wafer during the semiconductor fabrication process. In this EDX method, an electron beam is radiated on a defect on a semiconductor wafer, and the energy dispersion (spectrum) of the X ray generated from a defective portion and the neighborhood thereof is analyzed to estimate the element composition of the foreign particles. Estimating the element composition of foreign particles is very important for specifying the source of the foreign particles and taking a protective measure against dust in the fabrication process.

FIG. 2 is a diagram showing an example of the X-ray spectrum radiated from a defective portion and the neighborhood thereof upon radiation of an electron beam on a defect on a semiconductor wafer. With reference to FIG. 2, an explanation will be given of the fact that an element can be identified by analyzing the X-ray spectrum.

The X-ray spectrum includes a continuous X ray and a characteristic X ray as shown in FIG. 2. The continuous X ray is an electromagnetic wave generated by the incident electron beam accelerated in the direction opposite to the direction of progression when it impinges on an object. The magnitude of energy lost by the impinging electrons is various, with the result that X rays having various energies are radiated. Upon impingement of electrons, the electrons around the atomic nucleus of the wafer obtain energy and are released out of the atomic nucleus. Then, an electron vacancy is formed in the trajectory of the atomic nucleus. The electrons in the outer shell having a higher energy level are trapped in this vacancy, and with the resulting extra energy, a characteristic X ray is generated. The energy level of the electrons is determined by the elements, and therefore the wavelength of the characteristic X ray radiated is determined by the elements. Thus, an element can be identified from the combination of the wavelengths of the characteristic X rays appearing in the spectrum.

The wavelength of the characteristic X ray has been studied for long time, and the wavelength of the characteristic X ray generated by electron transition between different energy levels has already been determined for each element in the periodic table. The conventional EDX analyzer has such a function that the wavelength of the characteristic X ray of each element is stored in a library and the wavelength of the characteristic X ray extracted from the X-ray spectrum is collated with the library thereby to display a corresponding element and the peak position of the spectrum. The user can thus estimate the elements contained in the portion irradiated with the X ray.

(2) Data Acquisition Procedure in EDX

FIG. 3 is a flowchart for explaining the data acquisition procedure for a defective portion in EDX. Now, this data acquisition procedure for the detective portion will be explained. The data acquisition procedure is conducted typically by the operator determining whether or not EDX is to be carried out or not while observing the external appearance of the defective portion of a semiconductor wafer as an image under microscope.

As shown in FIG. 3, the data acquisition for the defective portions is carried out by repeating, for each defect, a series of steps including (1) loading a semiconductor wafer, (2) moving the stage to a defective portion, (3) confirming the external appearance of the defective portion, (4) determining whether EDX is to be carried out or not, and (5) carrying out EDX. As an alternative, in the case where images of defective portions are collected beforehand using an automatic defect reviewing device, the operator confirms the images collected, selects a defective portion to be subjected to EDX, and carries out the EDX detection process for the selected defective portion.

In connection with the foregoing description, a programming method for selecting a defective portion based on the size and type of foreign particles from a list of foreign particles detected by an inspection apparatus is described in JP-A-10-27833, etc.

(3) Protective Measure Based on EDX Data

FIG. 4 is a diagram for explaining a method of estimating the characteristic X ray unique to an element contained in a defect in actual analysis. Now, with reference to FIG. 4, an explanation will be given of a method of estimating the characteristic X ray unique to an element contained in a defect.

In analyzing foreign particles on a product wafer (process wafer), the fact that the X-ray spectrum contains the characteristic X rays generated from the defect or the neighborhood thereof and a lower layer pattern sometimes makes it difficult to estimate the characteristic X ray unique to the element contained in the defect. In actual analysis, therefore, as shown in FIG. 4, for example, the operator detects the X-ray spectrum of the reference portion of an adjoining chip, and by visually comparing the X spectrum of the reference portion with that of the detective portion, estimates the composition of the element contained in the defective portion. Further, the operator estimates the cause of the defect based on the defect composition.

As described above, the operator estimates the composition of the element contained in a defective portion and the cause of the defect by estimating the characteristic X ray unique to the element contained in the defect. In taking a protective measure against the defect, the operator is required to have a sufficient knowledge about the composition of a defect which may occur in each process and each fabrication unit through which a product wafer has been processed. Generally, therefore, it is not easy to estimate the cause of a defect.

SUMMARY OF THE INVENTION

The problems of the conventional techniques described above will be explained below.

(1) Number of Steps for Selecting an Object of EDX Analysis

Analysis of a defective portion using EDX requires a long time. Specifically, the time required for collecting data on one point is much longer than the time required for the foreign particle inspection apparatus or the defective reviewing device. For examples, assume the presence of 600 defects on a semiconductor wafer having a diameter of 300 mm. The time required for defect detection by a foreign particle inspection apparatus is several minutes for the whole wafer surface, and the time required for collecting the images of all the defects by the defect reviewing device is one hour or two in total. The collecting the X-ray spectra of all defects due to EDX, on the other hand, requires at least several days. Thus, it is unrealistic to apply EDX for all the defects on a semiconductor wafer.

Before carrying out EDX, therefore, it is necessary to manually select defects to be subjected to EDX from among the defects found by the inspection apparatus. However, the problem is that this defect selecting process consumes considerable labor. In the case where the work described with reference to FIG. 3 is conducted sequentially on each defect detected by the inspection apparatus, the operator is required to be engaged in the measurement work for long time. In the case where the images of defective portions are collected in advance by the automatic defect reviewing device, on the other hand, the image re-detection is not required but it is necessary for the EDX operator to confirm the images collected and to select defects subjected to EDX at the same time. This still poses the problem that many fabrication steps are required.

(2) Estimation of Defect Composition for Process Wafer

The method of analyzing the composition of the defective portion according to the prior art described with reference to FIG. 4 poses the problems described below.

(a) The peak of the characteristic X ray attributable to the bedding or a lower layer pattern of the wafer cannot be identified automatically. As a result, the operator is required to conduct the work of comparing the spectra of the defective portions and the spectrum of the reference portion, thereby requiring a long time for the comparison work.

(b) Long time is required for detecting the X-ray spectrum of the reference portion.

(c) Even though the elements contained in the defective portion can be estimated, the information required for coping with the defect cannot be obtained directly. To take a protective measure against defects, it is necessary to introduce the past defect cases and the protective measures taken against them and to study the process to which the product of the particular type is subjected. Thus, it is not always easy to estimate the cause of a defect.

(3) X-ray Spectrum Detection Time

The analysis of the defective portion using EDX requires a long time. Specifically, the time required for collecting data for each point is very long as compared with the corresponding time for the foreign particle inspection device or the defect reviewing device. The EDX often requires about one or two minutes to collect the X-ray spectrum for each defect.

(4) Reduction of Objects of EDX Analysis

There is no conventional method available for reducing the number of objects of EDX analysis to the required minimum. JP-A-10-27833 described above fails to disclose a method of removing, from the list of defects detected by the inspection apparatus, the defect sources requiring no analysis such as a detection error and a pattern defect erroneously detected by the inspection apparatus. Also, this patent publication contains no description about a method of selecting a representative one of defects for each defect type, e.g. selecting one largest defect for each defect type. Nor the same patent publication deal with any method of selecting a defect according to general defect features such as height, size or brightness.

The object of the present invention is to solve the above-mentioned problems of the prior art, and to provide a defect inspection apparatus and a defect inspection method in which a defect generated on a semiconductor process wafer is classified rapidly and reliably based on the external appearance and the composition thereof thereby to facilitate the execution of the protective measure against the cause of the defects.

In order to achieve the object of the invention described above, according to one aspect of the invention, there is provided a defect inspection apparatus comprising:

an X-ray spectrometer of energy dispersion type;

means for analyzing a detected defect image acquired through a secondary electron detector and calculating the image features of the defect;

a user interface for inputting the criterion (sampling rule) for determining whether the X-ray detection is to be carried out not for the image features of the defect; and a control computer for collating the image features output from the defect image analysis means with the criterion input for selecting the defects and giving an instruction to carry out the X-ray detection for a defect in keeping with the defect selection criterion.

According to another aspect of the invention, there is provided a defect inspection apparatus comprising: an X-ray spectrometer of energy dispersion type;

means for analyzing the X-ray spectrum detected and determining the peak position of the characteristic X ray;

means for storing the reference data including the X-ray spectrum of the defective portion, the peak position of the characteristic X ray determined by the spectrum analysis means and the detected defect image;

means for collating the peak position of the characteristic X ray determined by the spectrum analysis means with that of the characteristic X ray of the reference data stored in the reference data storage means and searching for the reference data having an analogous peak position; and a display screen for displaying the defect image and the X-ray spectrum of the reference data searched by the reference data search means.

According to still another aspect of the invention, there is provided a defect inspection apparatus comprising:

an X-ray spectrometer of energy dispersion type;

means for extracting the features of the element composition from the X-ray spectrum detected;

means for extracting the features of the detected image generated by the image generating means; and means for classifying defects based on the composition features extracted by the composition feature extraction means and the image features extracted by the image feature extraction means.

According to yet another aspect of the invention, there is provided a defect inspection method using an X-ray spectrometer of energy dispersion type, comprising the steps of;

inputting a criterion for determining whether the X-ray detection is to be carried out or not based on the image features of a defect;

collating the calculated defect image features with the criterion; and detecting the X ray from the defect of an object satisfying the criterion.

Other objects, features and advantages of the invention will become apparent from the following description of the embodiments of the invention taken in conjunction with the accompanying drawings.

BRIEF DESCRIPTION OF THE DRAWINGS

FIG. 7 is a diagram showing a screen for inputting the inspection conditions.

FIG. 8 is a diagram for explaining the concept of the automatic defect classification process.

FIG. 17 is a diagram showing an example of the screen for displaying a combination of the classification result by composition analysis and the classification result by image.

DESCRIPTION OF THE EMBODIMENTS

A defect inspection apparatus and a defect inspection method according to an embodiment of the invention will be explained in more detail below with reference to the drawings.

Figure 6:
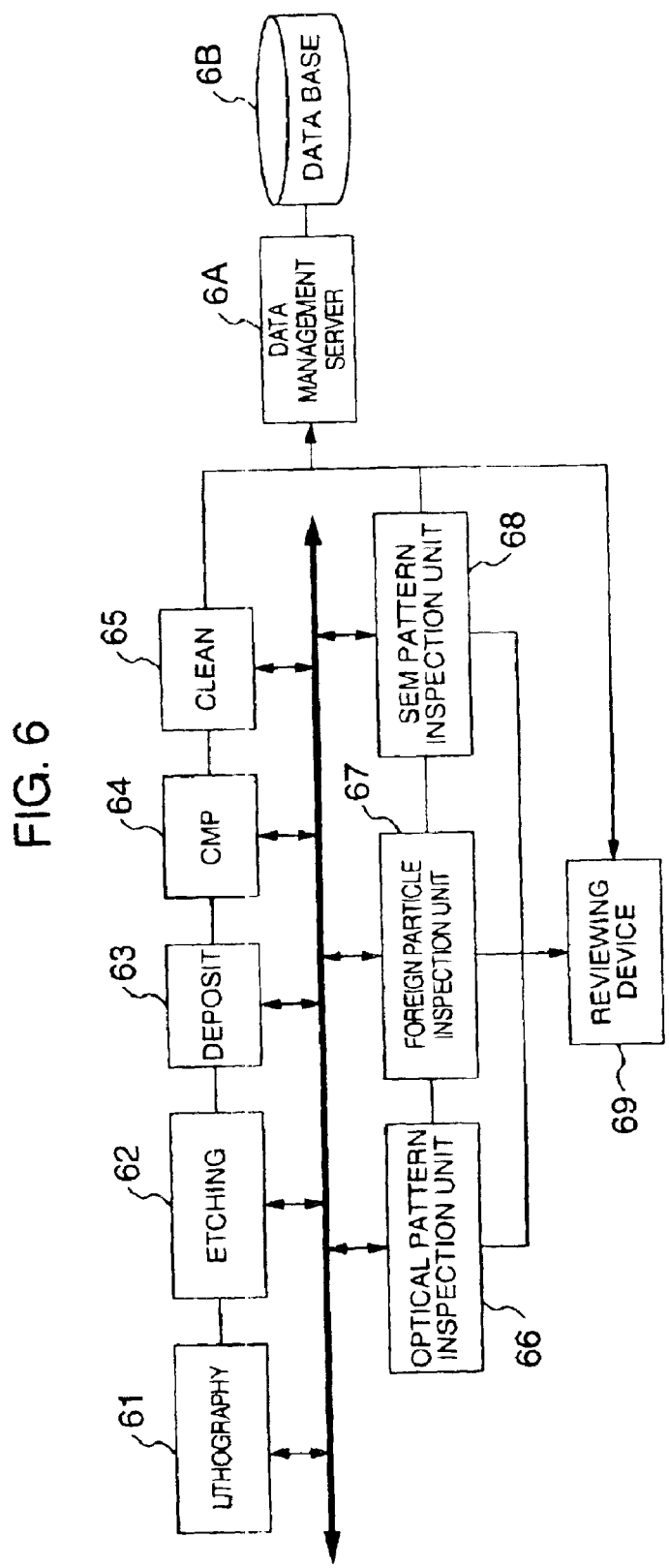
FIG. 6 is a diagram for explaining an outline of the semiconductor fabrication process including an inspection apparatus (reviewing device) according to an embodiment of the invention.

FIG. 6 is a diagram for explaining the concept of the semiconductor fabrication process including an inspection apparatus (reviewing device) according to an embodiment of the invention. In FIG. 6, reference numeral 61 designates a lithography step, numeral 62 an etching step, numeral 63 a deposition (film forming) step, numeral 64 a polishing (chemical mechanical polishing (CMP)) step, numeral 65 a cleaning step, numeral 66 an optical pattern inspection unit, numeral 67 a foreign particle inspection unit, numeral 68 a SEM pattern inspection unit, numeral 69 a reviewing device, numeral 6A a data management server, and numeral 6B a data base.

The semiconductor fabrication process, as shown in FIG. 6, includes the lithography step 61, the etching step 62, the deposition step 63, the polishing step 64, the cleaning step 65 and the inspection step. In some cases, there are as many as several hundred steps in total. Various inspection units are used for the inspection step according to the object involved. The inspection units used include the optical pattern inspection unit 66 for inspecting whether a pattern defect is generated or not after etching, the foreign particle inspection unit 67 for inspecting whether foreign particles are generated or not after deposition (forming a film), and the SEM pattern inspection unit 68 for detecting a minute pattern defect. The various fabrication units for executing these steps are connected by LAN. The processing conditions of the semiconductor wafer are transferred to the data management server 6A through the LAN, and information on the steps of processing the semiconductor wafer is accumulated for each lot or wafer. Also, the defect coordinate data detected by various inspection units are transferred, together with the inspection conditions, to the data management server through the LAN and registered in the data base 6B.

The inspection unit (reviewing device) 69 is for reviewing (analyzing) in detail the defects detected by the various inspection units described above. The reviewing device 69 receives, through the LAN, the defect coordinate data detected by the various inspection units, and subjecting the defect position thereof to the automatic defect review (ADR) with an electron beam image of high magnitude, makes it possible to observe the detective portion in detail. At the same time, the detected defect image is processed for measurement of the defect size and automatic defect classification (ADC). The reviewing device 69 also analyzes the element composition (EDX) of the detective portion by analyzing the spectrum of the X ray generated by electron beam radiation. Further, by referring to the wafer processing route information accumulated in the data management server, a candidate for the device that has caused the defect is displayed to support the analysis of the defect cause by the operator.

Next, the job sequence for the reviewing device 69 will be briefly explained. Before reviewing, the operator sets the conditions for executing ADR/ADC (hereinafter referred to as the ADR/ADC execution conditions) and the conditions for executing EDX (hereinafter referred to as the EDX execution conditions). The review execution conditions include the conditions for detecting the electron beam image. The EDX execution conditions include the conditions for selecting the defects to be detected by EDX and the conditions for detecting the X ray. The operator loads the wafer to be inspected in the apparatus, and after setting the ADR/ADC conditions and the EDX conditions, gives a review start instruction.

The reviewing device 69 detects the image of the defect to be reviewed, according to an instruction, and performs the process for calculating the defect feature amount and classifying the defects (ADR/ADC) by image processing. Then, in the case where there is a selected defect to be detected by EDX, the EDX is executed. The detected image and the X-ray spectrum are registered in the data base 6B.

Figure 5:
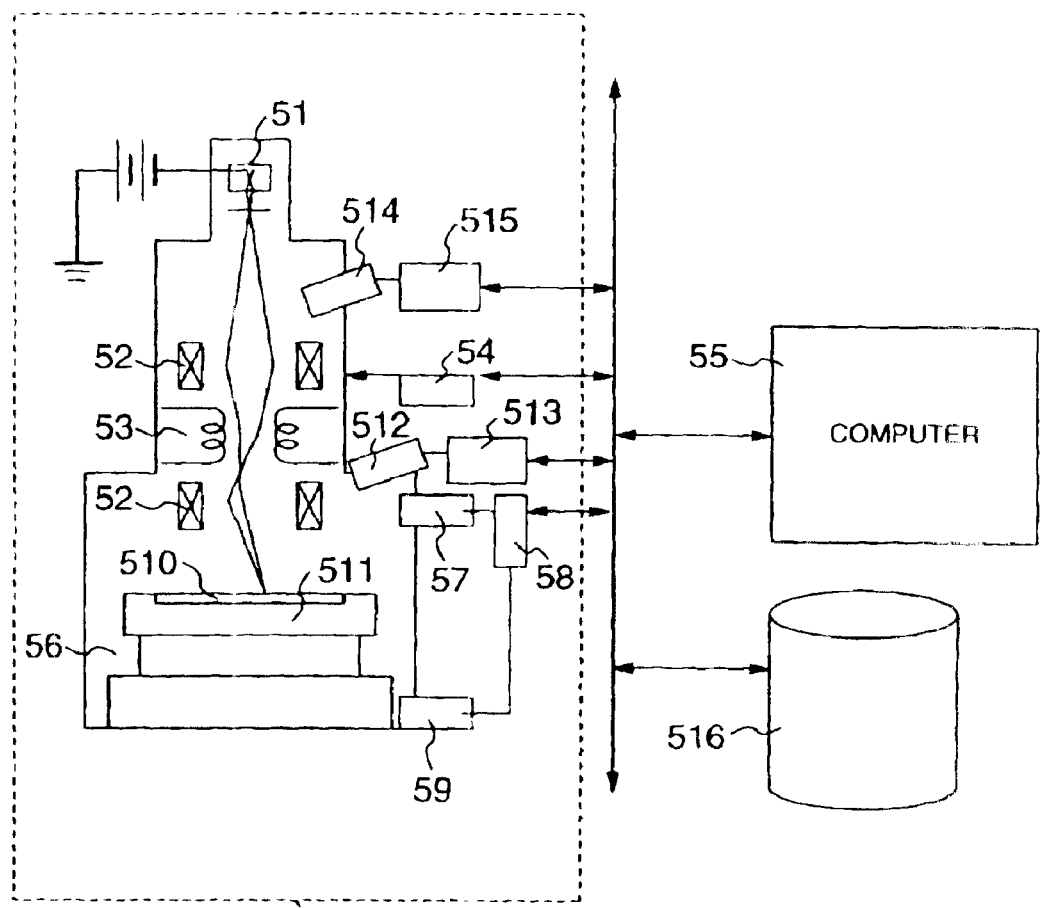
FIG. 5 is a block diagram showing a configuration of a reviewing device according to an embodiment of the invention.

FIG. 5 is a block diagram showing a configuration of a reviewer. In FIG. 5, numeral 51 designates an electron gun, numeral 52 an electron lens, numeral 53 a deflection system, numeral 54 a deflection system control circuit, numeral 55 a control computer, numeral 56 a sample chamber, numeral 57 a vacuum system, numeral 58 a vacuum control circuit, numeral 59 an oil-sealed rotary pump, numeral 510 an object to be inspected, numeral 511 a work holder, numeral 512 an X-ray spectrometer, numerals 513, 515 a signal processing circuit, numeral 514 a secondary electron detector, numeral 516 a storage unit, and numeral 518 an electron beam image/X-ray detection system.

The reviewing device 69 shown in FIG. 5 is configured of the electron beam image/X-ray detection system 518, the control computer 55 and the storage unit 516.

[1] Electron Beam Image/X-Ray Detection System

The electron beam image/X-ray detection system 518 radiates an electron beam on the object of inspection 510, and forms a secondary electron image by detecting the secondary electrons generated from the object, or forms an X-ray spectrum signal by detecting the X ray generated from the object. The electron beam image/X-ray detection system 518 is configured of a sample chamber 56, various detectors, a signal processing circuit, a control circuit, etc. The devices making up the electron beam image/X-ray detection system 518 will be explained below.

The electron gun 51 is made up of a filament heated for emitting thermal electrons, a Wehnelt cathode for converging the electrons which otherwise might diverge, and an acceleration electrode (anode) for accelerating the converged electron beam. The thermal electrons emitted from the filament are accelerated toward the anode by the voltage of the bias electric field applied to the Wehnelt cathode.

The electron lens 52 is for reducing the size of the electron source (electron beam) to several tens of Angstrom on the sample. As shown in simplistic way in FIG. 5, the electro-optic system normally includes two or three stages, in which the electron lens for the electron gun is called the convergence lens and the lens for the sample the objective lens.

The deflection system (such as a deflection coil) for radiating the electron beam in deflected way is controlled by the control computer 55 through the deflection system control circuit 54 thereby to scan the electron beam spot two-dimensionally on the object substrate to be inspected.

The sample chamber 56 has mounted therein a vacuum gauge 57 and is maintained in vacuum by being exhausted using the oil-sealed rotary pump 59 in compliance with a command from the vacuum control circuit 58. A sample 510 to be inspected such as a semiconductor circuit substrate is mounted and held on a work holder 511 in the sample chamber 56.

The secondary electron detector 514 is for detecting the secondary electrons emitted from the surface of the substrate upon radiation of the electron beam thereon. Specifically, in the secondary electron detector 514, the primary electrons scan the wafer so that the secondary electrons are generated from the wafer surface. These secondary electrons are detected by being collected through the interior of the lens by the lens magnetic field. The detection signal of the secondary electron detector is amplified in the signal processing circuit 515, and after being A/D converted, transferred to the control computer 55 through a bus.

The X-ray spectrometer 512 outputs an electrical signal corresponding to the energy of the X-ray quantum radiated from the wafer making up the sample to be inspected. This detection signal is amplified in the signal processing circuit 513, and after being A/D converted, is transferred to the control computer 55 through a bus.

[2] Control Computer

The control computer 55 has various functions including (a) a user interface (I/F) for inputting inspection conditions, (b) the function of controlling the electron beam image/X-ray detection system, (c) the function of processing the waveform data of the detection image and the X-ray signal, and (d) the function of displaying the detection image and the signal, and a data base. These functions will be sequentially explained below.

(a) User I/F for Inputting the Inspection Conditions

FIG. 7 is a diagram showing an input screen of the inspection conditions. With reference to this diagram, the inspection conditions will be explained. The inspection conditions include the following.

(i) Object of Inspection

The type, process, lot number, wafer number, etc. are designated. Based on the conditions thus designated, the control computer inquires the data management server of the information on the wafer to be inspected, and downloads the defect coordinate data, the processing start date and the like information through the LAN.

(ii) Detection Conditions

These conditions include the imaging magnification of the secondary electron image, the acceleration voltage of the electron beam, the probe current and the electron beam radiation diameter. Different conditions can be set for the detection of secondary electrons and the detection of EDX.

(iii) Operating Conditions

The conditions in general for executing ADR/ADC and EDX are set. The conditions include the defect detection sensitivity of ADR and the designation as to whether AF (Auto Focus) is executed or not.

(iv) EDX Sampling Conditions

This is a screen for setting the conditions for selecting the defects for which EDX is executed, from among the defects detected by the inspection apparatus. The user designates the select conditions based on the ID, size and type of the defect, as follows.

Condition 1: Select the defects of designated ID.

Condition 2: Select only the defects with the feature amount in a designated range.

Condition 3: Select only the defects with the feature amount in designated order of size.

Condition 4: Select only the designated defect type.

Condition 5: Conditions defined by a combination of the logical product, logical sum and negation of at least one of the conditions 1 to 4.

The conditions 2 and 3 described above are for selecting a defect based on the feature amount calculated by the image processing based on the external appearance of the defect in the ADR/ADC execution stage. The feature amount is defined as the size of a defect, for example. The diameter of a typical electron beam for EDX is on the order of $\mu$m, while the diameter of a foreign particle defect on the semiconductor wafer to be analyzed is at least on the order of several tens of nm. Thus, an area other than the defect is unavoidably included in the electron beam radiation area. On the other hand, the larger a defect, the larger the proportion of the component of the EDX signal from the defective portion, and therefore the EDX data or the result of processing thereof is expected to increase in reliability, or the EDX signal may be obtained within a shorter time. For this reason, only those defects of a predetermined size or larger can be designated as an object of EDX.

The condition 4 described above is for selecting a defect based on the result of classification of defects by ADR/ADC. Defects are classified, for example, into a round foreign particle, an acicular crystal, a cubic crystal or a scratch and a pattern open or pattern short.

According to the conditions described above, the following conditions for selection can be designated. In this case, assumed that the defects can be classified into a foreign particle type A, a foreign particle type B, a foreign particle type C, a pattern defect, a nuisance detection or detection error and an unknown defect according to ADC, as follows.

Selection condition 1: One each defect of maximum size is selected from each of the foreign particle type A, the foreign particle type B and the foreign type C, and ADR/ADC/EDX are executed.

Selection condition 2: One each defect of a size not less than 3 µm is selected from each of the foreign particle type A, the foreign particle type B and the foreign type C, and ADR/ADC/EDX are executed.

Selection condition 3: Only ADR/ADC is executed but not EDX for the pattern defect, the scratch defect and the detection error.

Selection condition 4: For all unknown defects, ADR/ADC/EDX are executed.

By designating the selection conditions described above, the operator can select any of the following modes: (1) EDX is intended to analyze the composition of a foreign particle defect, and therefore is not carried out for the pattern defect, the scratch defect or the detection error (selection condition 3); (2) The unknown defect is always analyzed in detail (selection condition 4); and (3) Even with regard to foreign particles, the requirement is sufficiently met by selecting a representative defect from each category (selection conditions 1 and 2).

(b) Function of Controlling the Electron Beam Image/X-Ray Detection System

In response to a review instruction issued by the operator through the user I/F for inputting the inspection conditions, the control computer 55 sets the electron beam image detection conditions in the electron beam image/X-ray detection system 518 and gives an instruction to detect an image. The electron beam image/X-ray detection system 518 moves the stage to the defect coordinate position based on the defect coordinate data of each defect and thus detects secondary electron images. The images thus detected are transferred to and stored in the control computer 55. Then, the control computer 55 sets the conditions for X-ray detection in the electron beam image/X-ray detection system 518 and gives an instruction for X-ray detection. The electron beam image/X-ray detection system 518 moves the stage based on the defect coordinate data for each defect designated in advance to be covered by EDX and detects the X ray. The X-ray spectrum thus detected is transferred to and stored in the control computer 55. The defects to be covered by EDX can be designated either before review or while checking the review images collected.

(c) Function of Processing Waveform Data of Detection Image and X-Ray Signal

FIG. 8 is a diagram for explaining the concept of the automatic defect classification process. With reference to FIG. 8, the function of processing the detected images and the waveform data of the X-ray signal will be explained.

The control computer 55 processes the detected defect images and automatically classifies the defects. First, N image feature amounts of the defect are calculated from a defect image and the image is set as a corresponding point in the N-dimensional space of the feature amount. The image feature amount includes the defect size, the geometric feature such as the roundness, the average value of brightness, the texture feature such as dispersion and the phase-related feature such as whether the defect is located on the bedding or the pattern in the image. The category classification of samples in correspondence with the feature amount space is a subject that has long been studied in the field of pattern recognition, and various methods are known. Some examples include a classification method based on whether a feature amount is included in a range predetermined by the user, and a method in which a distribution model (for example, N-dimensional normal distribution) in the feature amount space is assumed and parameters (including the mean vector and the variance/covariance matrix for the N-dimensional normal distribution) included in the distribution model are estimated using a teaching defect image thereby to determine a discriminant function.

With the functions described above, the reviewing device 69 automatically collects and classifies the images of defects. Thus, EDX can be carried out efficiently only for the defects meeting the conditions designated in advance by the operator.

It was explained above that the conditions for selecting the defects to be subjected to EDX are set before review according to an embodiment of the invention. According to the invention, however, the conditions for selecting the defects to be subjected to EDX can be set alternatively while checking the review image after ADR/ADC.

Figure 9:
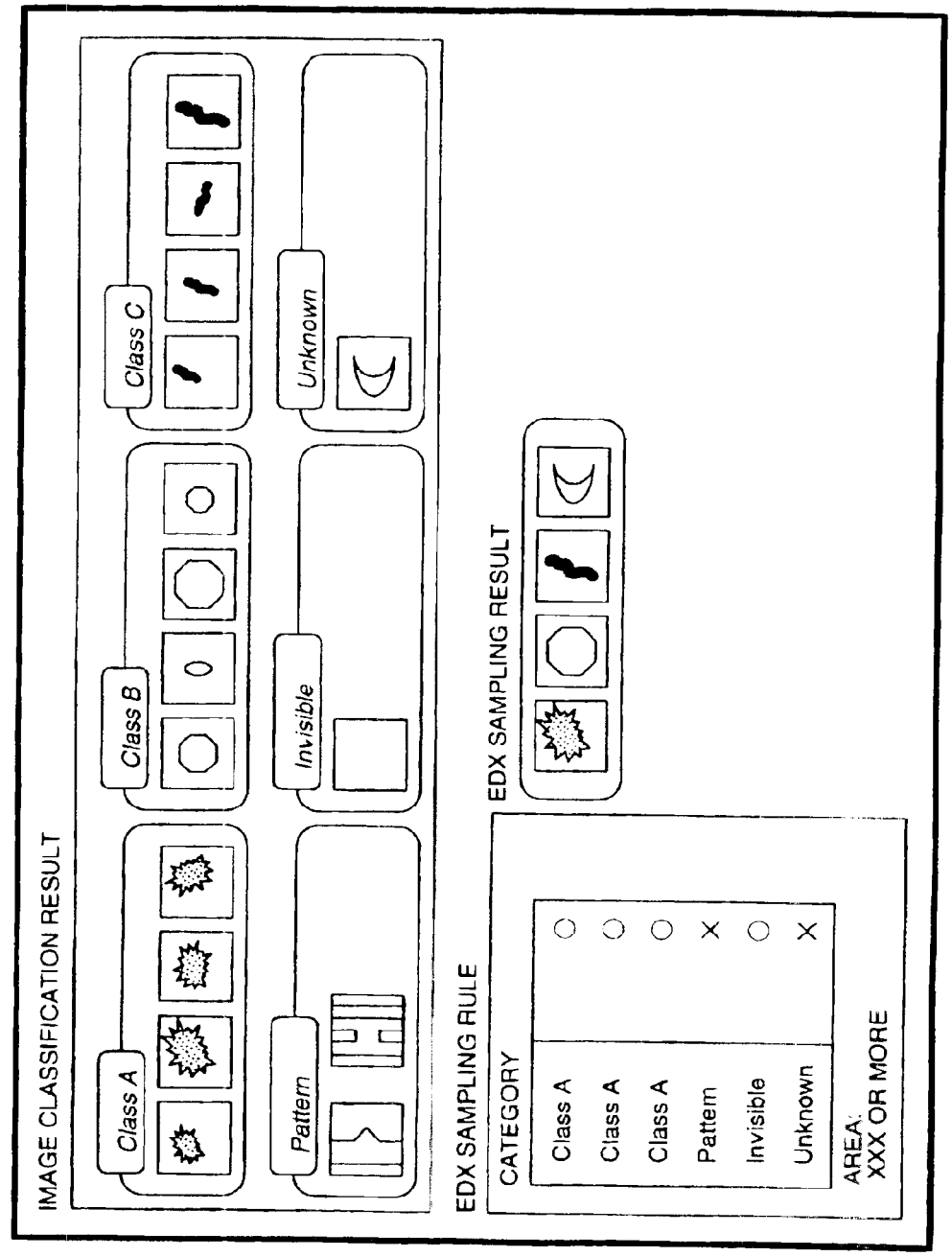
FIG. 9 is a diagram showing an example of a screen for setting the conditions for selecting defects to be subjected to EDX.

FIG. 9 is a diagram showing an example of a screen for setting the conditions for selecting the defects to be subjected to EDX. The use of this setting screen makes it possible to determine the selection conditions while checking the review image classification result and therefore an efficient selection is realized.

Figure 10:
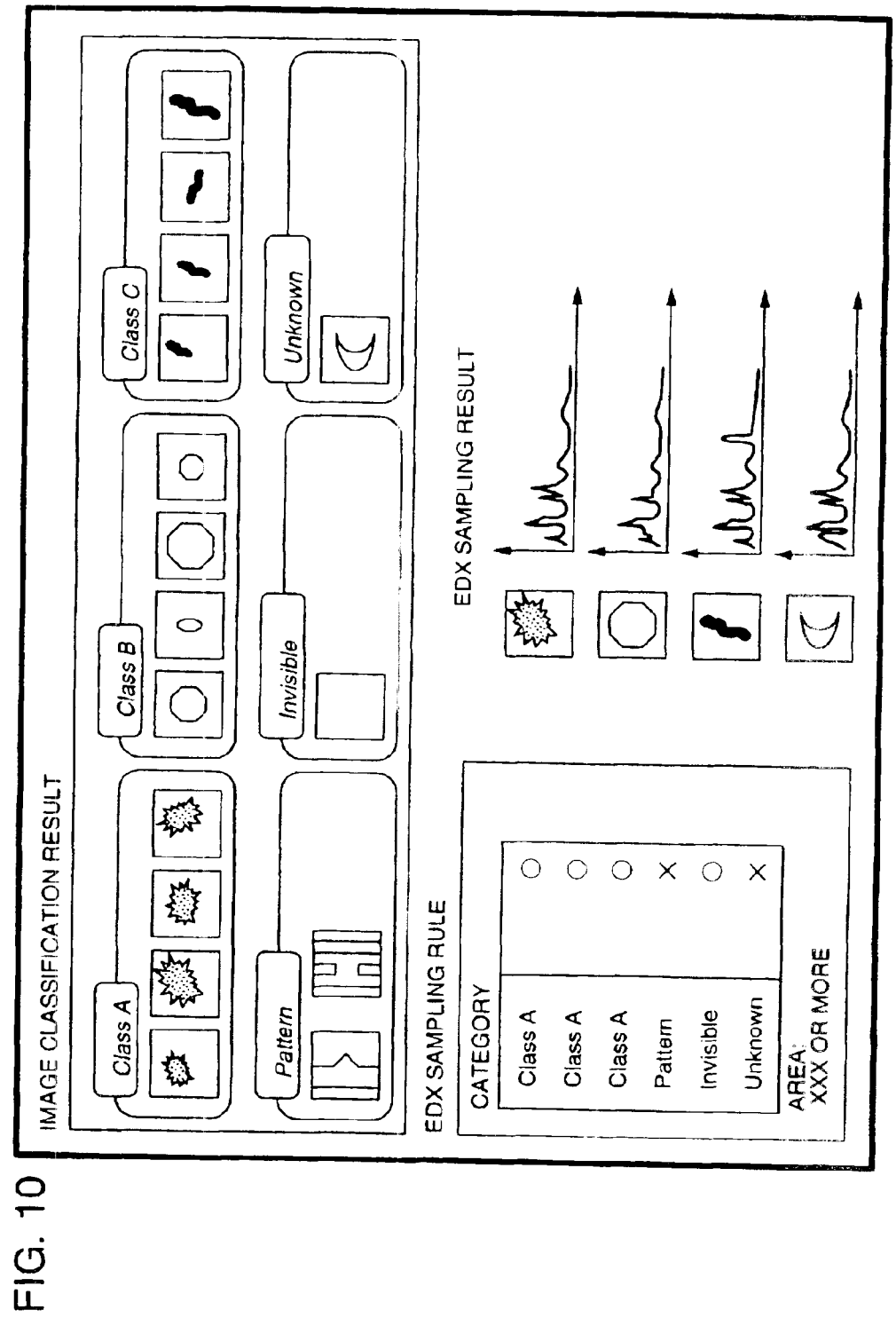
FIG. 10 is a diagram showing an example for displaying, in one display screen, the detected images automatically collected (ADR), the result of automatic classification (ADC) of the detected images and the result of the X-ray spectrum (EDX) detection.

(d) Function of Displaying Detection Images and Signals, and the Data Base Function FIG. 10 is a diagram showing an example in which the detection images collected automatically (ADR), the result of automatic classification (ADC) of the detection images and the result of detection of the X-ray spectrum (EDX) are displayed in a single display screen.

The operator can observe the image and the EDX at the same time on the display as shown in FIG. 10, and consequently can analyze a defect rapidly and accurately. These detected data and the processing result are registered in the data base of the storage unit 516.

Now, a second embodiment of the invention will be explained. According to the second embodiment of the invention, defects are classified and the cause of the defects estimated by EDX or by using both EDX and the image at the same time. The second embodiment described below has a similar hardware configuration to the first embodiment but is different from the first embodiment in the method of processing the detection signal and the configuration of the data base. In the second embodiment of the invention, the foreign particle information unique to the fabrication system having a dummy wafer (face plate wafer) for system management are collected and registered as reference information for defect classification.

Figure 1:
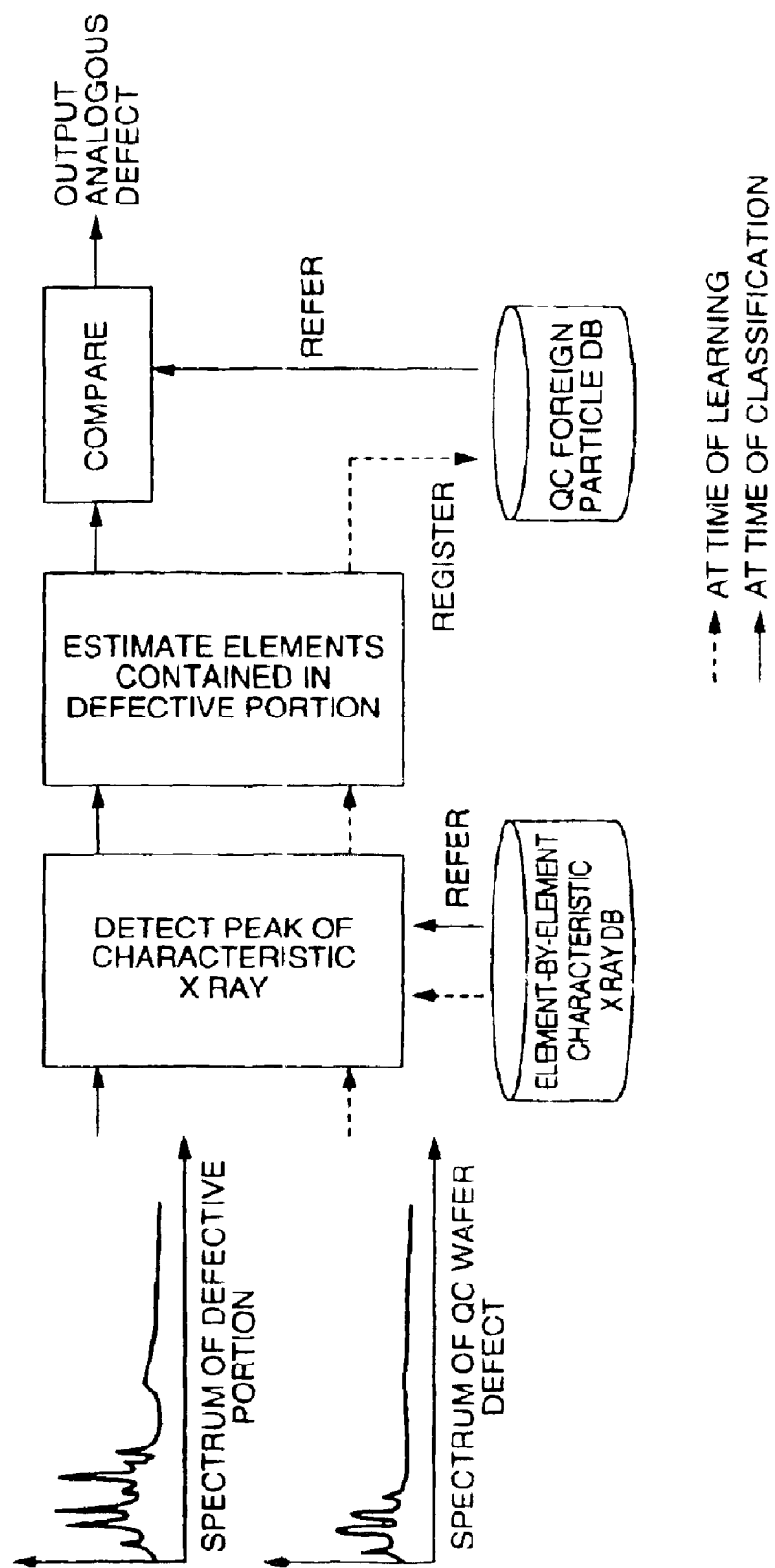
FIG. 1 is a flowchart for explaining the operation for processing a detection signal according to a second embodiment of the invention.
Figure 2:
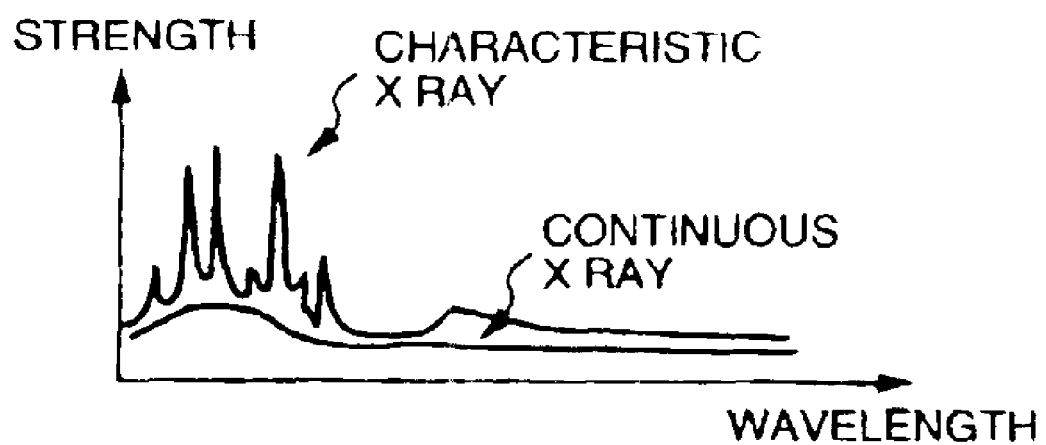
FIG. 2 is a diagram showing an example of the X-ray spectrum emitted from a defective portion and the neighborhood thereof when an electron beam is radiated on a defect of a semiconductor wafer.
Figure 3:
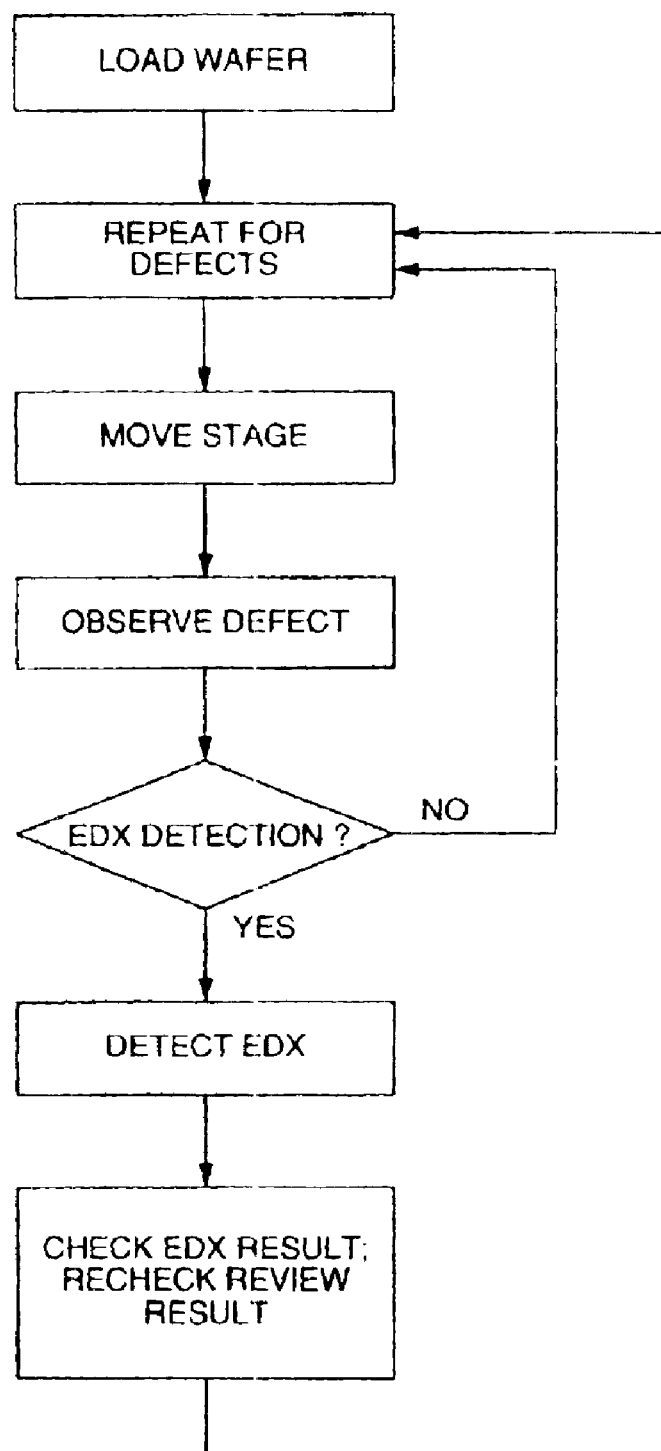
FIG. 3 is a flowchart for explaining the steps of acquiring data on the defective portion according to the conventional EDX.
Figure 4:
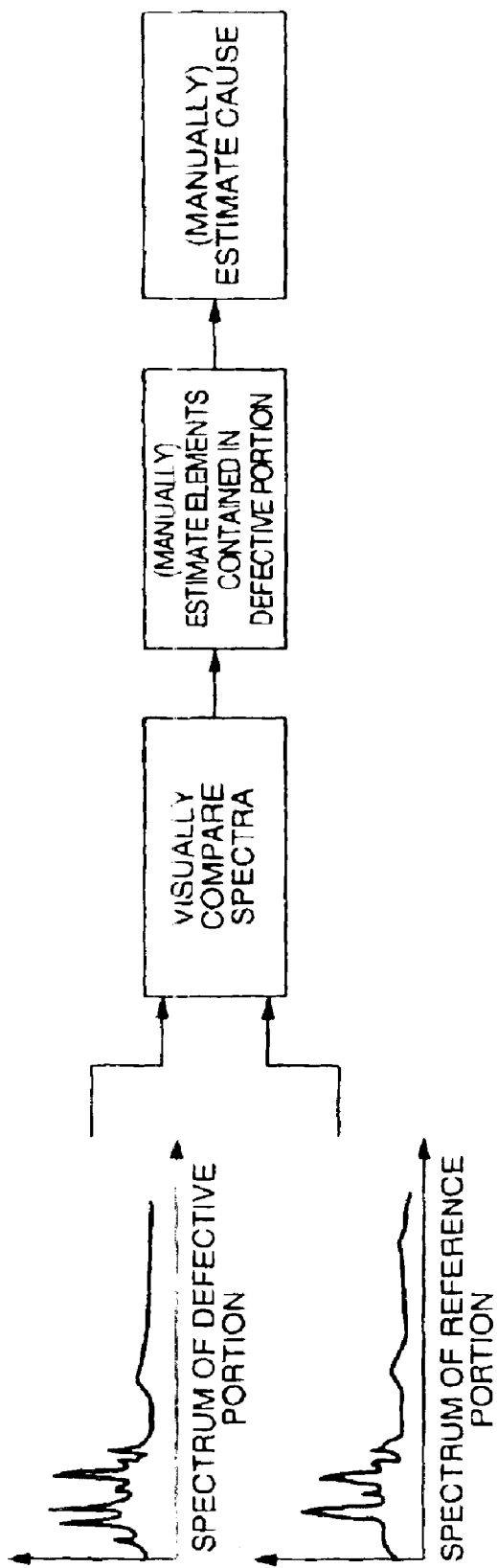
FIG. 4 is a diagram for explaining the conventional method of estimating the characteristic X ray unique to an element contained in a defect in actual analysis.

FIG. 1 is a flowchart for explaining the operation of processing the detection signal according to the second embodiment of the invention. With reference to FIG. 1, the processing operation will be briefly explained. The process is configured of two stages including learning and classification.

(Learning)

At the time of learning, the element composition of the foreign particles on the process QC wafer (the wafer charged on the line for the purpose of monitoring the fabrication system) is registered in the foreign particle data base for QC.

The correspondence between each element and the wavelength of the characteristic X ray unique to the particular element is incorporated beforehand as a data base of the characteristic X rays for each element.

(Step 1: Extraction of Peak Position of Characteristic X Ray)

Te X-ray spectrum of a defective portion is detected, and the peak position of the characteristic X ray is extracted from the X-ray spectrum.

Figure 11:
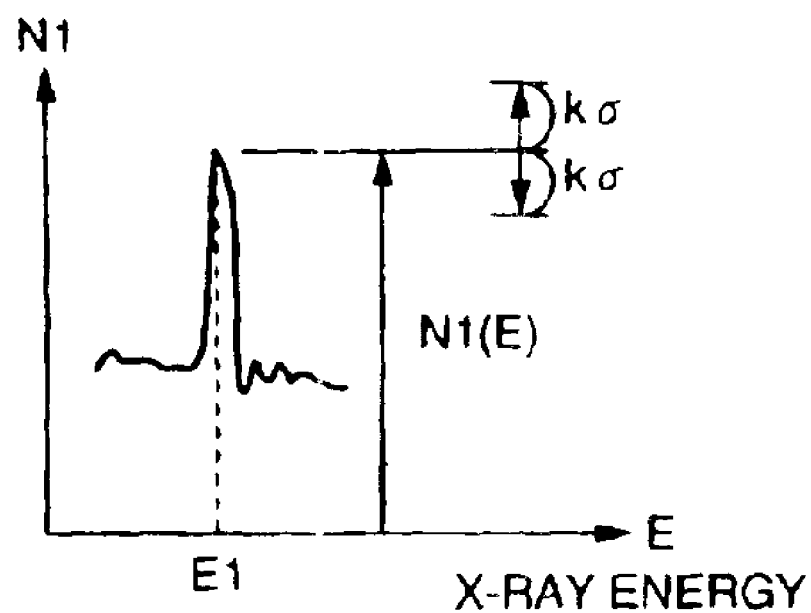
FIG. 11 is a diagram for explaining a method of extracting the peak position of the characteristic X ray from the X-ray spectrum.

FIG. 11 is a diagram for explaining a method of extracting the peak position of the characteristic X ray from the X-ray spectrum. As shown in FIG. 11, the X-ray spectrum is obtained as an X-ray energy and the X-ray quantum count N1 (E) corresponding to the particular energy. It is known that the process of releasing the X-ray quantum can be obtained in a model as a Poison process, and that in the case where the count of the continuous X rays registered in advance is N2 (E) for each energy, for example, the standard deviation $\sigma$ is estimated as $\sqrt{N2}$ (E). By determining whether the count N1 (E) is included in the reliability range of 100* $(1-\alpha)\%$ of the continuous X rays, therefore, the strength of the characteristic X ray can be determined. In the foregoing description, $\alpha$ can be set as a parameter in advance by the operator or built in the system in advance.

(Step 2: Estimation of Elements Contained in Defective Portion)

By collating the extracted peak position with the character X-ray data base by element, the elements contained in the defective portion are estimated. This estimation can be carried out by employing a method in which assuming that the extracted peak positions are given as $\{Pi:i=1\ldots,N\}$, the elements having each peak $\{Pi\}$ of the characteristic X ray can be comprehensively listed at the time of collation with the data base X.

(Step 3: Registration in Foreign Particle Data Base for QC (Quality Control))

The information for specifying a defect (type, process, wafer number, defect ID, etc.), the detection signal and the analysis result (type of elements estimated to be contained, the X-ray spectrum and detection image) are registered in the foreign particle data base for QC. As an alternative, the defects may be registered with the category assigned to them.

(Classification)

(Step 1: Extraction of Peak Position of Characteristic X Ray)

The peak position of the characteristic X ray is extracted from the X-ray spectrum of a defect to be inspected.

(Step 2: Estimation of Elements Contained in Defective Portion)

The elements contained in the defective portion are estimated by collation with the data base in which the wavelength of the characteristic X ray of each element is registered.

(Step 3: Comparison)

The foreign particle defects for QC registered in the foreign particle data base for QC are searched for a defect having the same element, which defect is displayed. More specifically, the defect having the same element(s) as those estimated in step 2 as being contained in the defective portion is searched from the defects registered in the foreign particle data base for QC and is displayed. In the absence of such a defect, a signal indicating the absence of analogous defects is output. As an alternative, a defect which contains an element(s) that is (are) partially in common or is same may be output. In the case where the defect category is also registered in the foreign particle data base for QC, on the other hand, the category assigned to the registered defect is output at the same time.

Figure 12:
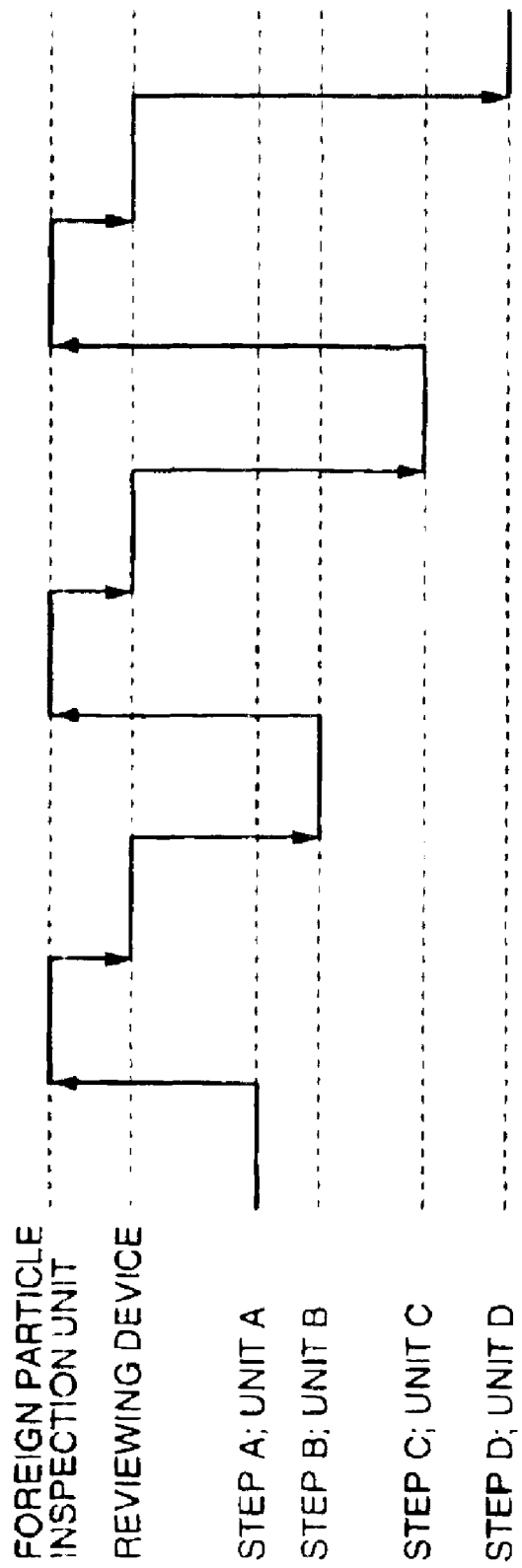
FIG. 12 is a diagram for explaining an example of the steps of registering the reference information on the process QC (Quality Control) wafer.

FIG. 12 is a diagram for explaining an example of the procedure for registering the reference information on the process QC wafer. With reference to FIG. 12, the procedure for registering the reference information for the process QC wafer will be explained. Each step of registering the reference information for the process QC wafer, as shown in the flowchart of FIG. 12, for example, is executed sequentially by the foreign particle inspection unit and the reviewing device. Normally, the inspection step is incorporated as an appearance inspection step once for every several to several tens of steps. The process QC wafer is inspected for defects by the foreign particle inspection unit following the completion of the process in the fabrication units A to D for executing the steps A to D shown in FIG. 12. The defects thus detected are reviewed by the reviewing device thereby to collect the images and the X-ray spectra. The defective models, the lot number, the wafer number, the image, the X-ray spectrum, the process of defect occurrence and the user defining category including the information obtained by the review are registered. The procedure described above completes the registration in the data base of the X-ray spectrum and the image information of the defects occurred in each step.

Figure 13:
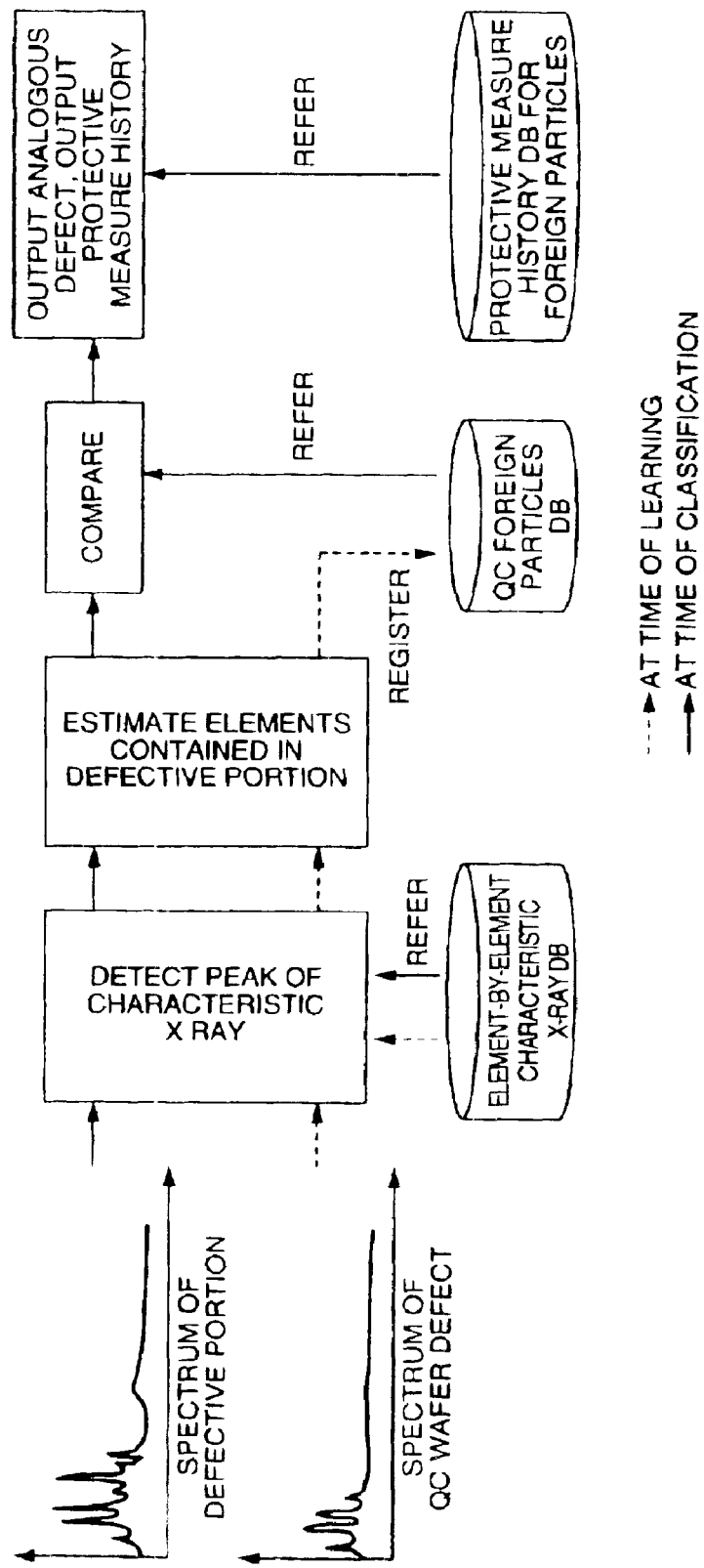
FIG. 13 is a flowchart for explaining the operation of processing the detection signals according to a modification of a second embodiment of the invention.

FIG. 13 is a flowchart for explaining the operation of processing the detection signal according to a modification of a second embodiment of the invention. This modification will be explained below.

The processing operation shown in FIG. 1 is different from that shown in FIG. 13 in that the processing operation shown in FIG. 13 makes it easy to take a protective measure against defects by searching and displaying the history of protective measures with reference to the data base of the history of the protective measures against foreign particles. The data base of the history of the protective measures against foreign particles has registered therein the information on the history of the protective measures taken against foreign particles generated in the past for each defect, including the wafer type, the process, the lot ID, the wafer ID, the defect ID and corresponding information on the protective measures (the defect sources, specific protective measures, dates at which the measures were taken, etc.).

Figure 14:
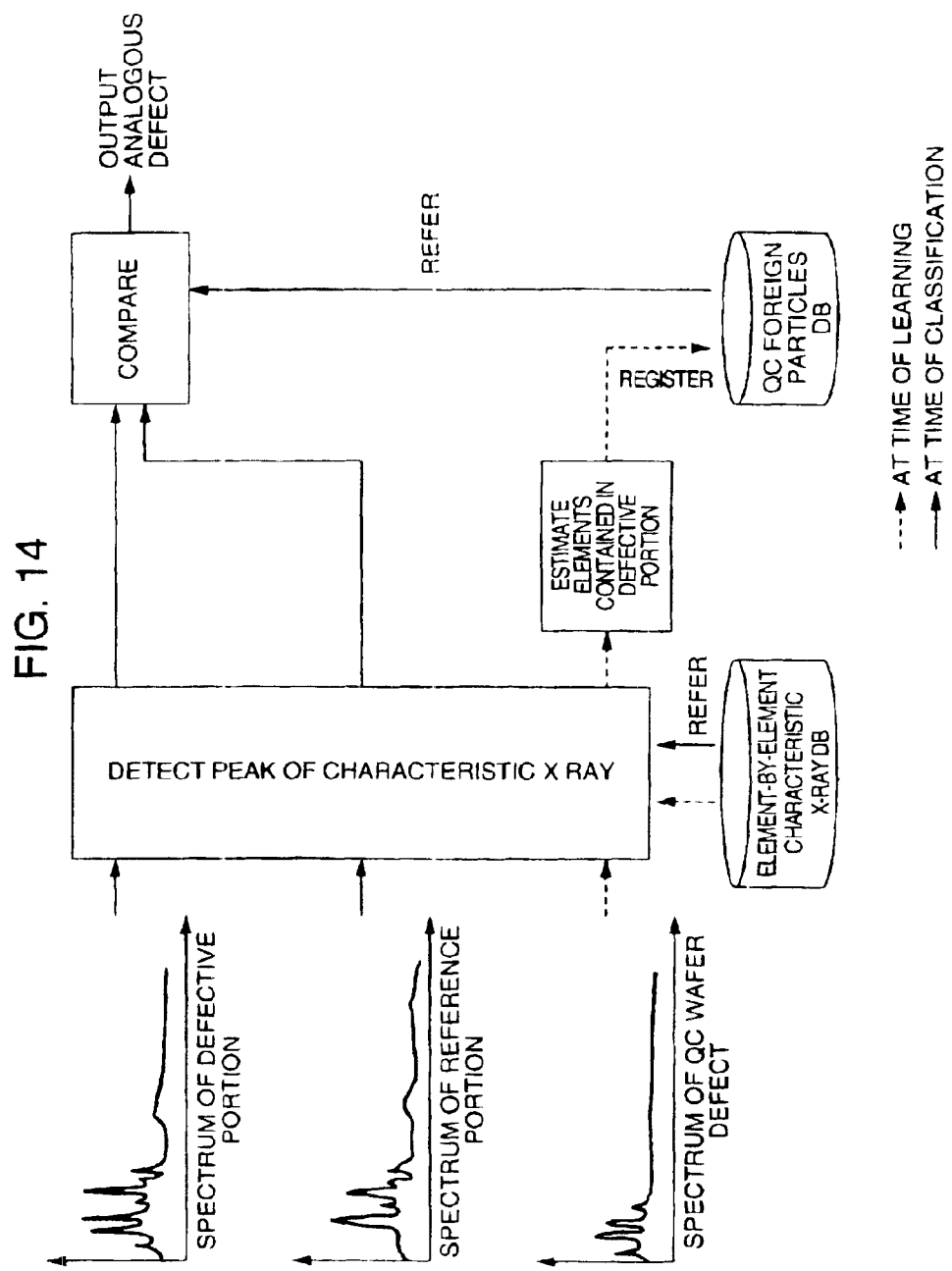
FIG. 14 is a flowchart for explaining the operation of processing the detection signals according to another modification of the second embodiment of the invention.

FIG. 14 is a flowchart for explaining the operation of processing the detection signal according to another modification of the second embodiment of the invention. This modification will be explained below.

The example of the processing operation shown in FIG. 14 is to detect the X-ray spectrum of the reference portion as well as that of the defective portion, and by using it for classification, to make possible a very reliable classification. Specifically, in this example, and the X-ray spectrum of the defective portion is detected, the peak position of the characteristic X ray is extracted from the X-ray spectrum. Then, the reference X-ray spectrum is detected, and the peak position of the characteristic X ray is extracted from the X-ray spectrum. Further, the peak positions of the characteristic X rays obtained from the defective portion and the reference portion are compared with each other.

In the case where comparison shows that a peak absent in the spectrum of the reference portion appears in the spectrum of the defective portion, the particular peak is regarded as the one unique to an element contained in the defective portion, and the element is estimated by reference to the characteristic X ray data base. In the case where comparison shows that the spectrum of the defective portion coincides with or is included in that of the reference portion, on the other hand, it is decided that the element contained in the defective portion is identical to the ions sputtered in the bedding, the pattern or the oxide film.

Further, in the example shown in FIG. 14, the defects registered in the foreign particle data base are searched for an analogous defect. As an alternative, the data base storing the past information on the history of protective measures against foreign particles may be searched.

Figure 15:
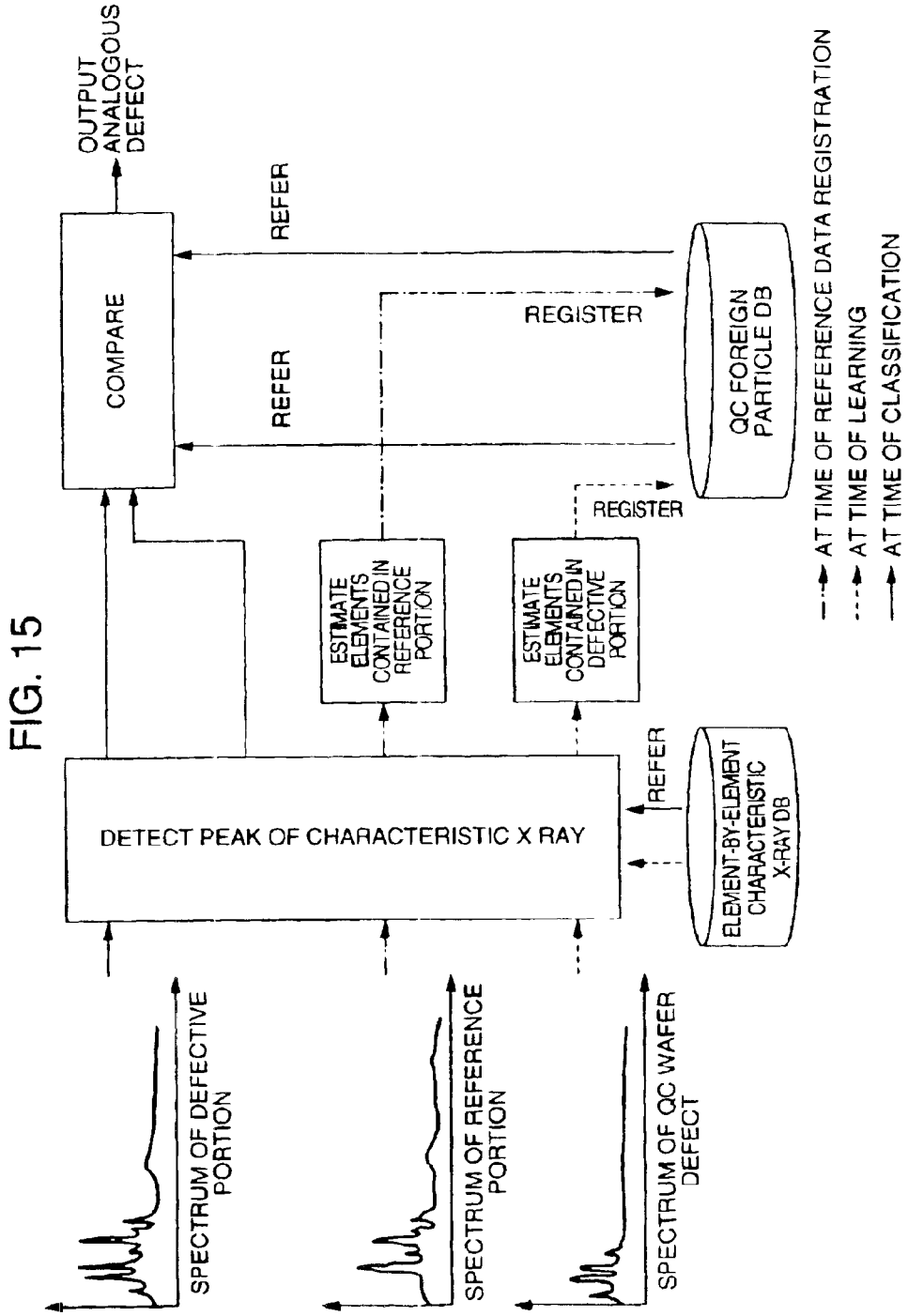
FIG. 15 is a flowchart for explaining the operation of processing the detection signals according to still another modification of the second embodiment of the invention.

FIG. 15 is a flowchart for explaining the operation of processing the detection signal according to still another modification of the second embodiment of the invention. This modification will be explained below.

The processing operation shown in FIG. 15 is different from that shown in FIG. 14 that in the processing operation shown in FIG. 15, the X-ray spectrum of the reference portion is registered. The X-ray spectrum of the reference portion is defined as the X-ray spectrum detected at a specific point on the wafer before review. Normal points are considered to have the same element composition, though somewhat different from one detection point to another. Once a reference X-ray spectrum is detected for each product type and step, therefore, the element composition of the normal points can be registered in advance before review.

Figure 16:
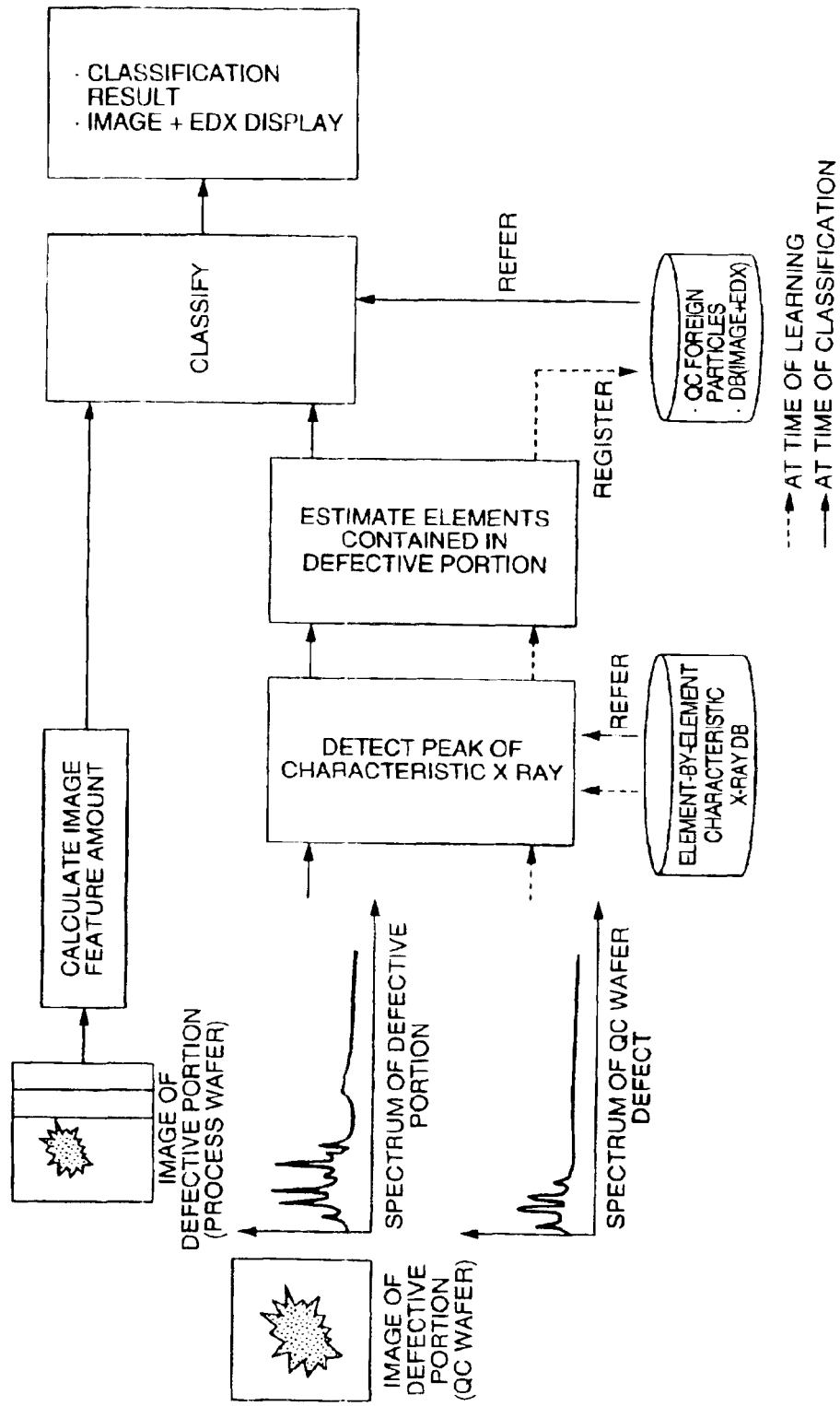
FIG. 16 is a flowchart for explaining the operation of processing the detection signals according to yet another modification of the second embodiment of the invention.

FIG. 16 is a flowchart for explaining the operation of processing the detection signal according to yet another modification of the second embodiment of the invention. This modification will be explained below.

The processing operation shown in FIG. 16 is different from that shown in FIG. 1 most significantly in that in the processing operation shown in FIG. 16, the automatic classification or the search is conducted using both the image information and the X-ray spectrum at the same time. Specifically, in the process shown in FIG. 16, the first step is to detect, at the time of learning, the X-ray spectrum of foreign particles on the process QC wafer and register it in the foreign particle data base as in the case explained with reference to FIG. 11. Then, at the time of classification, the X-ray spectrum of the defective portio is detected and the composition of the elements is estimated. At the same time, the feature amount of the image is also calculated by detecting the image of the defective portion. Next, the classification is carried out based on the element composition and the image feature amount. Assuming that the element composition is one of the feature amounts, the general classification and search method explained in the first embodiment is applicable.

As a modification of the example described above, the result of classification by composition analysis and the result of classification by image can be combined with each other.

FIG. 17 is a diagram showing an example of the screen for displaying the classification result by composition analysis and the classification result by image combined.

In FIG. 17, "Class 1" and "Class 2" indicate the classification according to the elements contained in the defect. Defects having the same element composition may present different appearance depending on the process of defect generation. The external appearance of the defect generated by reaction in gas phase, for example, is different from that of the defect caused when a reaction product attached to the inner wall of the chamber drops. For taking a protective measure against defects, therefore, it is desirable to determine the dust generating process according to the external appearance of a defect as well as the dust-generating process based on the element composition of the defect.

On the other hand, "Class A" and "Class B" indicate the classification based on the external appearance of defects. Defects having an analogous external appearance may have different compositions. Foreign particles generated in a different fabrication apparatus, for example, may assume a spherical shape due to the reaction in gas phase. In taking a protective measure against defects, therefore, it is desirable to estimate the dust-generating apparatus according to the element composition as well as the defect classification based on the appearance.

The portions covered by both the classification of Class 1, Class 2 and Class A, Class B indicate a combination of the classification result by composition analysis and the classification result by image described above. The operator can estimate the dust source and the dusting process by observing the classification result based on the X-ray spectrum and the image information.

As described above, the operator can change and optimize the EDX execution conditions dynamically according to the classification result indicated. Conditions for executing EDX include the acceleration voltage, for example. The higher the acceleration voltage, the broader the area in which the electron beam expands in the sample, thereby leading to the trend to generate the X rays from a wider area. Also, the higher the acceleration voltage, the larger the tendency toward a higher S/N, i.e. a higher ratio of the detection intensity of the characteristic X ray to that of the continuous X ray. As long as the X-ray detection area is not excessively large as compared with the size of the object of measurement, i.e. the defect size, therefore, the acceleration voltage is desirably higher. In accordance with the defect size, therefore, the acceleration voltage is changed.

As explained above, the embodiments of the invention implement (2) to (5) of the following functions by the inspection apparatus constituting the reviewing device according to the invention: (1) the inspection function to detect the defect position from above the wafer to be inspected, (2) the defect review/automatic classification function to re-detect and classify the image at the defect position, (3) the sampling function to select the object of EDX analysis based on the review result, (4) the EDX function to subject the selected defect to EDX analysis, and (5) the function to collectively process the EDX analysis result and the image review result. Nevertheless, according to the invention, the functions of the inspection system including the inspection units can be shared in any other appropriate way.

Some examples of the manner in which the functions of the inspection system are shared are: (I) to mount all the functions of (1) to (5) above on the inspection apparatus constituting a reviewing device, (II) to mount the function (1) on a corresponding inspection unit, the functions (2) and (3) on an inspection unit constituting a reviewing device, the function (4) on the analyzer, and the function (5) on the inspection server, and (III) to mount the function (1) on a corresponding inspection unit, the functions (2), (3) and (5) on an inspection unit constituting a reviewing device, and the function (4) on the analyzer.

According to the embodiments of the invention, the number of steps for selecting the object to be subjected to EDX analysis can be reduced and the EDX can be executed efficiently. Specifically, the detection error made by the inspection apparatus and the pattern defects erroneously detected by the inspection apparatus can be removed automatically from the objects of EDX analysis. Also, the largest defect can be selected for each defect type, or otherwise a representative defect to be subjected to EDX analysis can be selected for each defect type. Further, defects can be selected according to ordinary defect features such as height, size or brightness.

In addition, the embodiments of the invention described above can reduce the number of steps of analyzing the composition of the defective portion of a process wafer and estimating the cause of the defects. Further, the composition of the defective portion of a process wafer can be analyzed with highly reliability. What is more, defects can be classified according to the composition and the external appearance thereof, thereby making it possible to easily and accurately determine the cause of the defects and the manner in which they are generated.

It will thus be understood from the foregoing description that according to the invention, the composition of the defective portion can be analyzed with higher rapidity based on the X-ray spectrum while at the same time easily and accurately determining the cause of the defects and the manner in which they are generated.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. A defect inspection apparatus comprising:
   an electro-optic system configured to radiate an electron beam on an object to be inspected;
   a secondary-electron detector configured to detect secondary electrons generated from the object in response to the electron beam, and from the secondary electrons to generate an electrical signal;
   an image generator configured to convert the electrical signal output from the secondary-electron detector into a digital image;
   a user interface configured to receive radiation conditions for radiating the electron beam in the electro-optic system;
   an electro-optic system controller configured to set the radiation conditions for radiating the electron beam in the electro-optic system;
   a defect-image analyzer configured to calculate image features of the object by analyzing the digital image;
   wherein the user interface is configured to receive defect-selection criterion used to determine whether an X-ray spectrum is to be detected for the object;
   a control computer configured to collate the image features output from the defect-image analyzer with the defect-selection criterion, and generate an instruction to initiate detection of the X-ray spectrum if the image features substantially match the defect-selection criterion;
   an energy distribution X-ray spectrometer configured to detect the X-ray spectrum of the object based on the instruction; and
   a monitor configured to display the X-ray spectrum adjacent to the digital image of the object for defect analysis.

2. The defect inspection apparatus according to claim 1,
   wherein the defect-image analyzer is configured to display on the monitor a set of category names respectively associated with a set of categories,
   wherein the categories include at least one of foreign particles, a pattern defect, a detection error and an unknown defect, and
   wherein if the object is associated with at least one of the categories, then the control computer is configured to generate the instruction to initiate detection of the X-ray spectrum.

3. The defect inspection apparatus according to claim 1,
   wherein the defect-image analyzer is configured to output a size of the object,
   wherein the size is at least one of the image features, and
   wherein the collation includes a collation of the size and the defect-selection criterion.

4. The defect inspection apparatus according to claim 1,
   wherein the control computer is configured to set the radiation conditions based on a defect-feature amount of at least one of the image features, and
   wherein the defect-feature amount is output from the defect-image analyzer.

5. A defect inspection apparatus comprising:
   an electro-optic system configured to radiate an electron beam on an object to be inspected;
   a secondary-electron detector configured to detect secondary electrons generated from the object in response to the electron beam and to generate an electrical signal from the secondary electrons;
   an image generator configured to generate a digital image of the object based on the electrical signal;
   an energy-dispersion X-ray spectrometer configured to detect an X-ray spectrum generated by the object in response to the electron beam;
   a user interface configured to receive a set of radiation parameters from a user, wherein the radiation parameters are for radiating the electron beam;
   an electro-optic system controller configured to set the radiation parameters for the electron beam;
   a composition-feature-extraction unit configured to extract a composition feature of an element composition from the detected X-ray spectrum;
   an image-feature-extraction unit configured to extract an image feature from the digital image; and
   a defect-classification unit configured to classify the object based on the composition feature and the image feature
   a monitor configured to substantially simultaneously display the X-ray spectrum and the digital image of the object for defect analysis.

6. A defect inspection method comprising the steps of:
   radiating an electron beam on an object;
   detecting secondary electrons generated by the object in response to the electron beam;
   generating a digital image based on the secondary electrons;
   calculating an image feature of the object by analyzing the digital image;
   collating the image feature with a criterion stored in a memory;
   based on the collating step, determining whether to generate an X-ray spectrum of the object;
   if a determination is made to generate an X-ray spectrum:
      changing a radiation condition for the electron beam;
      subsequent to the changing step, radiating the electron beam on the object;
      detecting an X-ray spectrum of the object in response to the step of radiating the electron beam on the object with the changed radiation condition; and
      displaying on a display the X-ray spectrum and the digital image for defect analysis of the object.

7. A defect inspection method comprising the steps of:
   radiating an electron beam having a first radiation condition on a wafer that includes a plurality of defects;

detecting secondary electrons generated from the wafer in response to the electron beam;

generating a plurality of digital images corresponding to the plurality of defects based on the detected secondary electrons;

calculating a plurality of image features that respectively correspond to the plurality of defects by analyzing the digital images;

based on the image features, selecting a defect from the plurality of defects for element analysis;

changing a radiation condition for the electron beam from the first radiation condition to a second radiation condition; thereafter radiating the electron beam on the select defect; and detecting an X-ray spectrum generated from the select defect in response to the electron beam;

adjacently displaying on a display the X-ray spectrum and the digital image of the select defect for analysis of the select defect.

8. The defect inspection method of claim 7, further comprising entering the second radiation condition using a user interface.

9. The defect inspection method of claim 7, further comprising entering a criterion for selecting the select defect using a graphical user interface displayed on a display.

\* \* \* \* \*